United States Patent
Mochizuki

(10) Patent No.: US 12,023,196 B2
(45) Date of Patent: Jul. 2, 2024

(54) ULTRASONIC DIAGNOSTIC APPARATUS AND STORAGE MEDIUM

(71) Applicant: CANON MEDICAL SYSTEMS CORPORATION, Otawara (JP)

(72) Inventor: Fumio Mochizuki, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 94 days.

(21) Appl. No.: 17/217,142

(22) Filed: Mar. 30, 2021

(65) Prior Publication Data

US 2021/0307720 A1    Oct. 7, 2021

(30) Foreign Application Priority Data

Apr. 3, 2020  (JP) .................. 2020-067533

(51) Int. Cl.
*A61B 8/08* (2006.01)
*A61B 8/00* (2006.01)

(52) U.S. Cl.
CPC ............ *A61B 8/0891* (2013.01); *A61B 8/463* (2013.01); *A61B 8/488* (2013.01); *A61B 8/5207* (2013.01); *A61B 8/5246* (2013.01)

(58) Field of Classification Search
None
See application file for complete search history.

(56) References Cited

U.S. PATENT DOCUMENTS

| | | | |
|---|---|---|---|
| 2017/0095226 A1* | 4/2017 | Tanaka | A61B 8/4416 |
| 2017/0196535 A1* | 7/2017 | Arai | A61B 8/466 |
| 2017/0213380 A1* | 7/2017 | Samset | A61B 8/0883 |
| 2017/0367587 A1* | 12/2017 | Ebata | A61B 8/06 |
| 2019/0328317 A1 | 10/2019 | Mochizuki et al. | |

FOREIGN PATENT DOCUMENTS

| | | |
|---|---|---|
| JP | A-2014-198240 | 10/2014 |
| JP | A-2015-177883 | 10/2015 |
| JP | 2017-74221 A | 4/2017 |
| JP | 2019-93140 A | 6/2019 |
| JP | 2019-118686 A | 7/2019 |
| JP | 2019-188005 A | 10/2019 |
| WO | WO 2005/006987 A1 | 1/2005 |

OTHER PUBLICATIONS

Japanese Office Action dated Sep. 5, 2023, issued in Japanese Patent Application No. 2020-067533.

* cited by examiner

*Primary Examiner* — Jonathan Cwern
(74) *Attorney, Agent, or Firm* — Oblon, McClelland, Maier & Neustadt, L.L.P.

(57) ABSTRACT

An ultrasonic diagnostic apparatus of an embodiment includes processing circuitry. The processing circuitry is configured to acquire a B mode image in which a signal intensity of reflected waves obtained in such a manner that ultrasonic waves are transmitted to a scanning area in a subject and reflected in the subject is represented by luminance levels, and a Doppler image of a region of interest included in the scanning area. The processing circuitry is configured to cause a display to display the Doppler image superposed on the B mode image acquired. In addition, the processing circuitry is configured to change a display mode of the Doppler image displayed on the display using a feature quantity obtained on the basis of at least one of the B mode image and the Doppler image in a time series acquired.

9 Claims, 7 Drawing Sheets

ULTRASONIC DIAGNOSTIC APPARATUS AND STORAGE MEDIUM

CROSS-REFERENCE TO RELATED APPLICATION

The present application claims priority based on Japanese Patent Application No. 2020-067533, filed on Apr. 3, 2020, the content of which is incorporated herein by reference.

FIELD

Embodiments disclosed in the present disclosure and drawings relate to an ultrasonic diagnostic apparatus and a storage medium.

BACKGROUND

As a recent technology supporting central vein paracentesis, an ultrasonic diagnostic apparatus that detects a position of a blood vessel that is a paracentesis target from color Doppler information on a central scanning line in an ultrasonic image, measures a distance from a probe surface to the center of the target blood vessel, and provides an ultrasonic image including measurement results is known. A practitioner can adjust the position of the probe such that the target blood vessel is depicted at the center of the image by measuring the distance from the target blood vessel (vein) to the surface of the probe using color Doppler information, and thus misreading of a depth of the blood vessel from the image can be curbed.

However, since an image based on color Doppler information is superposed on a region in a blood vessel in a step of puncturing a target blood vessel with a paracentesis needle, there are cases in which the visibility of a tool such as the paracentesis needle deteriorates.

DETAILED DESCRIPTION

An ultrasonic diagnostic apparatus of an embodiment includes processing circuitry. The processing circuitry is configured to acquire a B mode image in which a signal intensity of reflected waves obtained in such a manner that ultrasonic waves are transmitted to a scanning area in a subject and reflected in the subject is represented by luminance levels, and a Doppler image of a region of interest included in the scanning area. The processing circuitry is configured to cause a display to display the Doppler image superposed on the B mode image acquired. In addition, the processing circuitry is configured to change a display mode of the Doppler image displayed on the display using a feature quantity obtained on the basis of at least one of the B mode image and the Doppler image in a time series acquired.

Hereinafter, an ultrasonic diagnostic apparatus and a storage medium of embodiments will be described with reference to the drawings.

Figure 1:
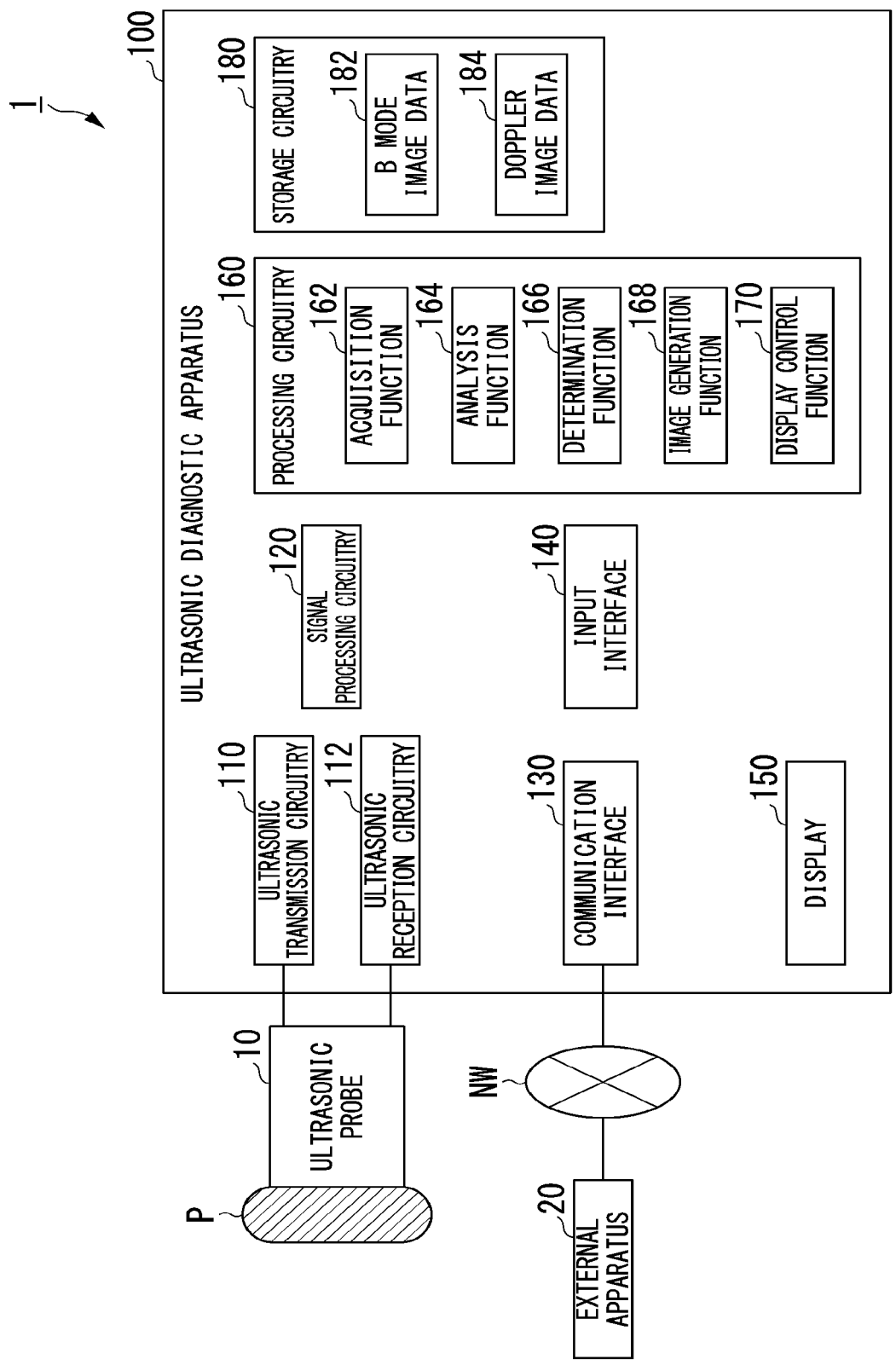
FIG. 1 is a configuration diagram of an ultrasonic diagnostic system including an ultrasonic diagnostic apparatus of an embodiment.

FIG. 1 is a configuration diagram of an ultrasonic diagnostic system 1 including an ultrasonic diagnostic apparatus 100 of an embodiment. The ultrasonic diagnostic system 1 includes an ultrasonic probe 10, an external apparatus 20 and the ultrasonic diagnostic apparatus 100. The external apparatus 20 and the ultrasonic diagnostic apparatus 100 may be connected, for example, through a network NW such as a wide area network (WAN), a local area network (LAN), the Internet, a dedicated line, a wireless base station, or a provider. The ultrasonic probe 10 may be included in the configuration of the ultrasonic diagnostic apparatus 100. The ultrasonic probe 10 is an example of a "probe."

For example, the ultrasonic probe 10 transmits ultrasonic waves to a scanning area in a living body P that is a subject to execute ultrasonic scanning according to control of the ultrasonic diagnostic apparatus 100. The ultrasonic probe 10 may include, for example, a plurality of piezoelectric vibrators, matching layers provided in the piezoelectric vibrators, a backing material for preventing backward propagation of ultrasonic waves from the piezoelectric vibrators, and the like. For example, the ultrasonic probe 10 may be a one-dimensional array linear probe having a plurality of ultrasonic vibrators arranged in a predetermined direction. The ultrasonic probe 10 may be detachably connected to the ultrasonic diagnostic apparatus 100 or a plurality of ultrasonic probes 10 may be connected to the ultrasonic diagnostic apparatus 100. When a plurality of ultrasonic probes 10 are connected to the ultrasonic diagnostic apparatus 100, which one of the connected ultrasonic probes will be used for ultrasonic scanning is arbitrarily selected by a switching operation of an operator or the like.

The external apparatus 20 may be, for example, a picture archiving and communication system (PACS) that is a system for managing various types of medical image data, an electronic medical chart system for managing electronic medical charts having medical images attached thereto, or the like. In addition, the external apparatus may be a storage apparatus such as a storage server or a database.

The ultrasonic diagnostic apparatus 100 may include, for example, ultrasonic transmission circuitry 110, ultrasonic reception circuitry 112, signal processing circuitry 120, a communication interface 130, an input interface 140, a display 150, a processing circuitry 160, and storage circuitry 180. The input interface 140 is an example of an "input." The display 150 is an example of a "display." The storage circuitry 180 is an example of a "storage."

The ultrasonic transmission circuitry 110 transmits a driving signal to the plurality of piezoelectric vibrators of the ultrasonic probe 10 to generate ultrasonic waves according to vibration of the piezoelectric vibrators. Accordingly, ultrasonic waves are transmitted from the surface (body surface) of the living body P in contact with the probe surface of the ultrasonic probe 10 to the inside thereof.

The ultrasonic reception circuitry 112 receives a signal obtained in such a manner that ultrasonic waves transmitted from the ultrasonic probe 10 are reflected by the tissues in the living body P, and a reflected signal (reflected wave signal) is received by the plurality of piezoelectric vibrators and converted into an electric signal. A reflected wave signal in a case where ultrasonic pulses transmitted to the inside of the living body P have been reflected by a surface of a blood flow or the cardiac wall which is moving depends on a velocity component in an ultrasonic wave transmission direction of a moving object according to the Doppler effect and undergoes frequency shifting. The ultrasonic reception circuitry 112 amplifies a reflected wave signal received by the ultrasonic probe 10 or converts the reflected wave signal into a digital signal. In addition, the ultrasonic reception circuitry 112 may generate a reception signal having a reflective component emphasized in a direction depending on a reception directivity by giving a delay time necessary to determine the reception directivity to digital signals and summing a plurality of digital signals given the delay time.

The signal processing circuitry 120 performs signal processing for generating ultrasonic data on the basis of a signal received by the ultrasonic reception circuitry 112. The ultrasonic data includes B mode data and Doppler data. For example, the signal processing circuitry 120 performs envelope detection processing and logarithmic amplification processing on a signal received by the ultrasonic reception circuitry 112 to generate B mode data in which a signal intensity is represented by a luminance level. In addition, the signal processing circuitry 120 generates B mode image data including B mode data on two-dimensional ultrasonic scanning lines (raster) in a scanning area. Further, the B mode image data may include, for example, luminance information based on an object such as a paracentesis needle in the scanning area in addition to luminance information based on a region in the body included in the scanning area. The B mode image data may include information on a time at which it is generated.

In addition, the signal processing circuitry 120 generates Doppler data that is extracted motion information based on the Doppler effect of a moving object in a region of interest (ROI) set in the scanning area by performing frequency analysis on the basis of the signal received by the ultrasonic reception circuitry 112. As motion information of a target (moving object) included in the scanning area, for example, the signal processing circuitry 120 may generate Doppler data by estimating the average velocity, the average variance value, the average power value, and the like at each of a plurality of sample points. Here, the moving object may be a blood flow, tissues such as the cardiac wall, a contrast medium, and the like, for example. For example, the signal processing circuitry 120 may generate Doppler data by estimating the average velocity of a blood flow, the average variance value of the blood flow, the average power value of the blood flow, and the like at each of a plurality of sample points as motion information of the blood flow (blood flow information). In addition, the signal processing circuitry 120 generates Doppler image data including Doppler data on two-dimensional ultrasonic scanning lines in the ROI on the basis of the generated Doppler data. The Doppler image data may include information on a time at which it is generated. Ultrasonic image data may include, for example, B mode image data and Doppler image data. Further, it is assumed that two-dimensional coordinate positions of the B mode image data and the Doppler image data are associated with each other.

The communication interface 130 may include, for example, a communication interface such as a network interface card (MC). The communication interface 130 is connected to the external apparatus 20 through the network NW and performs data communication with the external apparatus 20.

The input interface 140 receives various input operations from an operator, converts a received input operation into an electric signal, and outputs the electric signal to the processing circuitry 160. For example, the input interface 140 may be realized by a mouse, a keyboard, a trackball, a switch, buttons, a joystick, a touch panel, or the like. In addition, the input interface 140 may be realized by a user interface that receives audio input, such as a microphone, for example. When the input interface 140 is a touch panel, the display 150 which will be described later and the input interface 140 may be integrated. Meanwhile, the input interface 140 in the present disclosure is not limited to components including physical operating parts such as a mouse and a keyboard. For example, an electric signal processing circuitry that receives an electric signal corresponding to an input operation from an external input device provided separately from the apparatus and outputs the electric signal to control circuitry is also included in examples of the input interface 140.

The display 150 displays various types of information. For example, the display 150 may display an image generated by the processing circuitry 160 according to control of a display control function 170 in a predetermined display mode or display a graphical user interface (GUI) or the like for receiving various input operations from an operator. For example, the display 150 may be a liquid crystal display (LCD), a cathode ray tube (CRT) display, an organic electroluminescence (EL) display, or the like.

The processing circuitry 160 may include, for example, an acquisition function 162, an analysis function 164, a determination function 166, an image generation function 168, and the display control function 170. The processing circuitry 160 may realize these functions, for example, by a hardware processor executing programs stored in a storage device (storage circuitry 180).

The hardware processor may refer to, for example, circuitry such as a central processing unit (CPU), a graphics processing unit (GPU), an application specific integrated circuit (ASIC), or a programmable logic device (e.g., a simple programmable logic device (SPLD) or a complex programmable logic device (CPLD), or a field programmable gate array (FPGA)). Programs may be directly incorporated in the circuit of the hardware processor instead of being stored in the storage circuitry 180. In this case, the hardware processor realizes functions by reading and executing the programs incorporated in the circuit thereof. The aforementioned programs may be stored in advance in the storage circuitry 180, or may be stored in a non-transitory storage medium such as a DVD or a CD-ROM and installed in the storage circuitry 180 from the non-transitory storage medium when the non-transitory storage medium is inserted into a drive device (not shown) of the ultrasonic diagnostic apparatus 100. The hardware processor is not limited to a configuration of a single circuit, and a plurality of independent circuits may be combined as a single hardware processor to realize each function. In addition, a plurality of components may be integrated into single hardware to realize each function. The acquisition function 162 is an example of an "acquirer." The analysis function 164 is an example of an "analyzer." The determination function 166 is an example of a "determiner" The image generation function 168 is an example of an "image generator." The display control function 170 is an example of a "display controller."

The storage circuitry 180 may be realized by, for example, a semiconductor memory element such as a random access memory (RAM) or a flash memory, a hard disk, an optical disc, and the like. These storage media including a non-transitory storage medium may be realized by other storage devices connected through the network NW, such as a network attached storage (NAS) and an external storage device. In addition, the storage circuitry 180 may include a transitory storage medium such as a read only memory (ROM) or a register. The storage circuitry 180 may store B mode image data 182, Doppler image data 184, programs, and other types of information, for example.

The acquisition function 162 acquires B mode image data and Doppler image data processed by the signal processing circuitry 120. In addition, the acquisition function 162 stores the acquired B mode image data and Doppler image data in the storage circuitry 180. B mode image data is stored in a time series in the B mode image data 182 stored in the storage circuitry 180 and Doppler image data is stored in a time series in the Doppler image data 184.

The analysis function 164 may derive a distance from the body surface to a blood vessel that is an example of a paracentesis target region (e.g., a distance from the body surface to a center position of the blood vessel), for example, by analyzing Doppler image data on a center raster of a scanning area. In addition, the analysis function 164 may derive the distance from the body surface to the center position of the blood vessel using B mode image data on the center raster of the scanning area.

In addition, the analysis function 164 may derive the distance from the body surface to the center position of the blood vessel by combining a Doppler image data analysis result and a B mode image data analysis result. In this case, the analysis function 164 may regard, for example, the average of a distance obtained from the Doppler image data and a distance obtained from the B mode image data as the distance from the body surface to the center position of the blood vessel. Meanwhile, a distance derived by the analysis function 164 is not limited to the distance from the body surface to the center position of the blood vessel, and a distance from the body surface to a position other than the center of the blood vessel (e.g., the surface of a blood vessel) may be derived. Further, a position at which a distance is derived is not limited to the center raster and other positions are available.

In addition, the analysis function 164 analyzes a feature quantity representing movement of the ultrasonic probe 10 on the basis of the time-series B mode image data 182 stored in the storage circuitry 180. This feature quantity may also be represented as, for example, a feature quantity indicating temporal variation in ultrasonic image data acquired by the ultrasonic probe 10. Processing in the analysis function 164 will be described in detail later.

The determination function 166 determines whether movement of the ultrasonic probe is stable with respect to a time axis on the basis of a result analyzed by the analysis function 164. Movement of the ultrasonic probe 10 is stable, for example, in a case where an amount of change in luminance information or the like between frames of time-series B mode images is not more than a predetermined amount. In addition, the determination function 166 may determine that movement of the ultrasonic probe 10 is stable, for example, even when an amount of change with respect to time in a distance from the body surface to a target region (e.g., blood vessel) obtained on the basis of Doppler image data is not more than a predetermined amount. That is, a state in which movement of the ultrasonic probe 10 is stable can be represented as a state in which B mode image data or Doppler image data is stable. In addition, if B mode image data and Doppler image data are commonly called an ultrasonic image, the determination function 166 determines whether an ultrasonic image is stable. Processing in the determination function 166 will be described in detail later.

The image generation function 168 generates an image for display to be displayed on the display 150 on the basis of B mode image data and Doppler image data. For example, the image generation function 168 may generate a B mode image for display based on B mode image data and a Doppler image based on Doppler image data. A B mode image may be, for example, an image obtained by converting information representing a luminance level at each coordinate position of B mode image data into a predetermined color or luminance on a color image. In addition, a Doppler image may be, for example, an image obtained by converting motion information of a moving object (e.g., the average velocity, the average variance value, the average power value, and the like of a blood flow) at each coordinate position of Doppler image data into a color, a pattern, or the like in response to the size of the motion information.

In addition, the image generation function 168 generates an image for display by superposing the Doppler image on an ROI included in the generated B mode image. In addition, the image generation function 168 may include, for example, information associated with the B mode image or the Doppler image, information analyzed by the analysis function 164, a scale, a body mark, and the like in the image for display. Furthermore, the image generation function 168 generates an image for display in which a Doppler image display mode has been changed on the basis of an instruction of the display control function 170.

The display control function 170 outputs the image generated in the image generation function 168 to the display 150. In addition, the display control function 170 determines a display mode of a Doppler image to be displayed on the display 150, for example, on the basis of details acquired by the acquisition function 162 and a result determined by the determination function 166 and causes the image generation function 168 to generate an image for display to be displayed in the determined display mode. Processing in the display control function 170 will be described in detail later.

Figure 2:
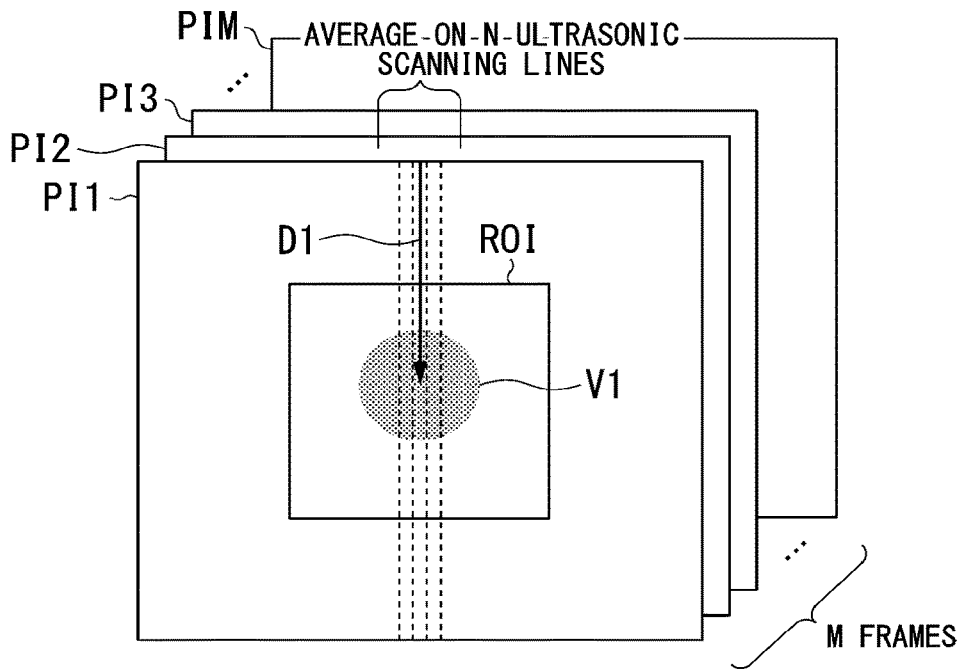
FIG. 2 is a diagram showing calculation of a distance from a body surface to a center position of a blood vessel using an analysis function.

Hereinafter, processing in the analysis function 164 will be described in detail. For example, the analysis function 164 may measure a distance from the body surface (the probe surface of the ultrasonic probe 10) to the center of a target (e.g., a blood vessel) using the Doppler image data 184. FIG. 2 is a diagram showing calculation of the distance from the body surface to the center position of a blood vessel by the analysis function 164. In the example of FIG. 2, ultrasonic images PI in which a region corresponding to a blood vessel V1 of the internal jugular vein is included in an ROI are shown. In addition, in the example of FIG. 2, M frames PI1, PI2, PI3, . . . , PIM of the ultrasonic images PI in a time series are shown. The analysis function 164 acquires average power values of blood flow on N ultrasonic scanning lines positioned near the center of a scanning area (within a predetermined distance from the center of the scanning area) with respect to the ultrasonic images PI shown in FIG. 2 and calculates an additional average of the acquired average power values. Next, the analysis function 164 stores additionally averaged average power values corresponding to the M frames and outputs a maximum value among the stored average power values corresponding to the M frames. In addition, when an additional average of a new average power value is calculated, the analysis function 164 deletes an oldest average power value and stores the new average power value. In the example of FIG. 2, average power values on scanning lines passing through the center of the blood vessel V1 positioned near the center of the scanning area are obtained. Then, the analysis function 164 outputs a maximum average power value among additionally averaged average power values in the M frames.

Figure 3:
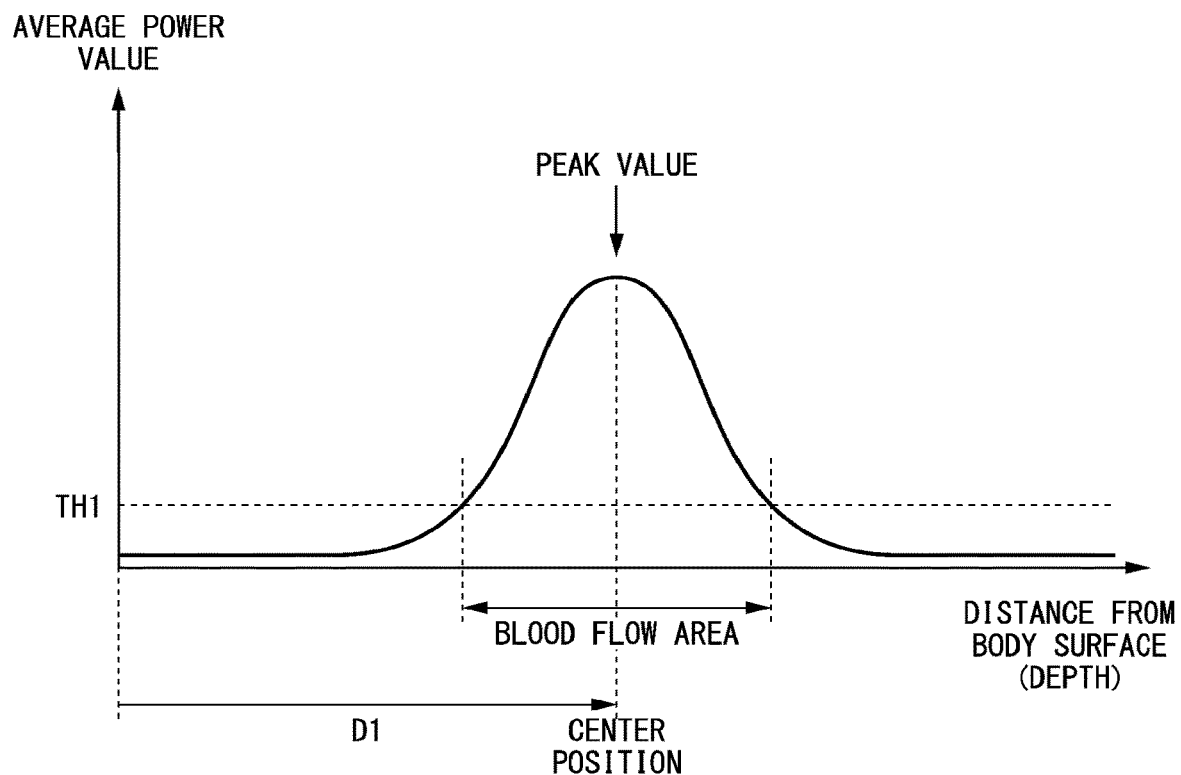
FIG. 3 is a diagram showing acquisition of a center position of a blood vessel area using the analysis function on the basis of the average power value.

FIG. 3 is a diagram showing acquisition of a center position of a blood vessel area by the analysis function 164 on the basis of average power values. In FIG. 3, the horizontal axis represents a distance (depth) from the body surface (probe surface of the ultrasonic probe 10) and the vertical axis represents the average power value of blood flow. The analysis function 164 acquires a part in which output average power values are equal to or greater than a predetermined first threshold value TH1 as a blood vessel area. In addition, the analysis function 164 extracts a peak value of average power values as a center position of the blood vessel. Then, the analysis function 164 derives a distance (depth) D1 from the probe surface (body surface) of the ultrasonic probe 10 to the center opposition of the blood vessel area.

Meanwhile, there may be a case in which parts corresponding to a plurality of blood vessels are placed on scanning lines positioned at the center part of a scanning area according to the position of the scanning area. In this case, the analysis function 164 may regard a blood vessel area closest to the probe surface of the ultrasonic probe 10 as a blood vessel that is a paracentesis target, for example.

Figure 4:
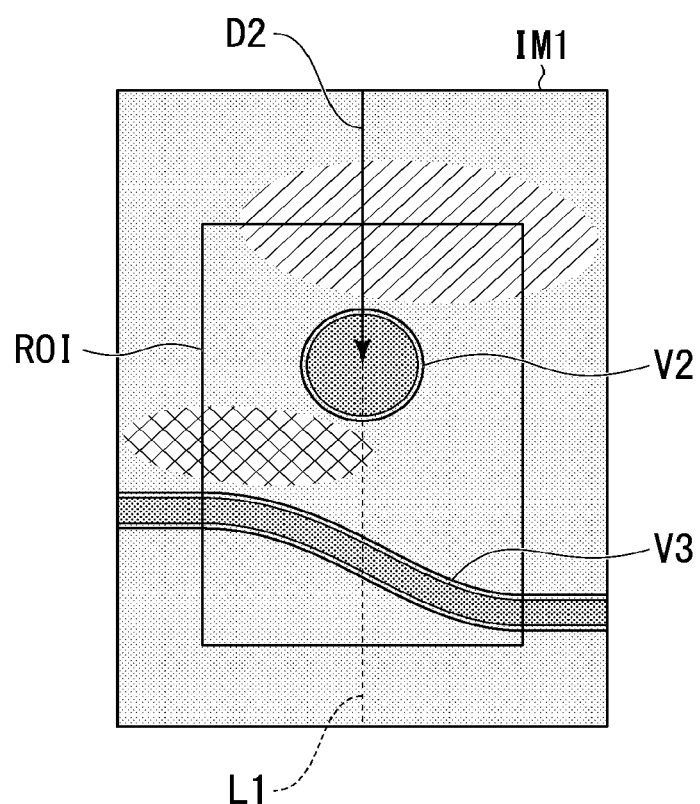
FIG. 4 is a diagram illustrating an example of a B mode image displayed on a display.

Meanwhile, the analysis function 164 may extract a blood vessel area using the B mode image data 182 instead of (or in addition to) extracting a blood vessel area using the Doppler image data 184. FIG. 4 is a diagram illustrating an example of a B mode image IM1 displayed on the display 150. In the example of FIG. 4, parts corresponding to two blood vessels V2 and V3 are included in an ROI of the image IM1. When a blood vessel area is extracted using B mode image data, the analysis function 164 may acquire luminance values on N ultrasonic scanning lines positioned at the center of a scanning area, for example. Next, the analysis function 164 calculates an additional average of the acquired luminance values on the N ultrasonic scanning lines and extracts a blood vessel area on the basis of the additionally averaged luminance value.

Figure 5:
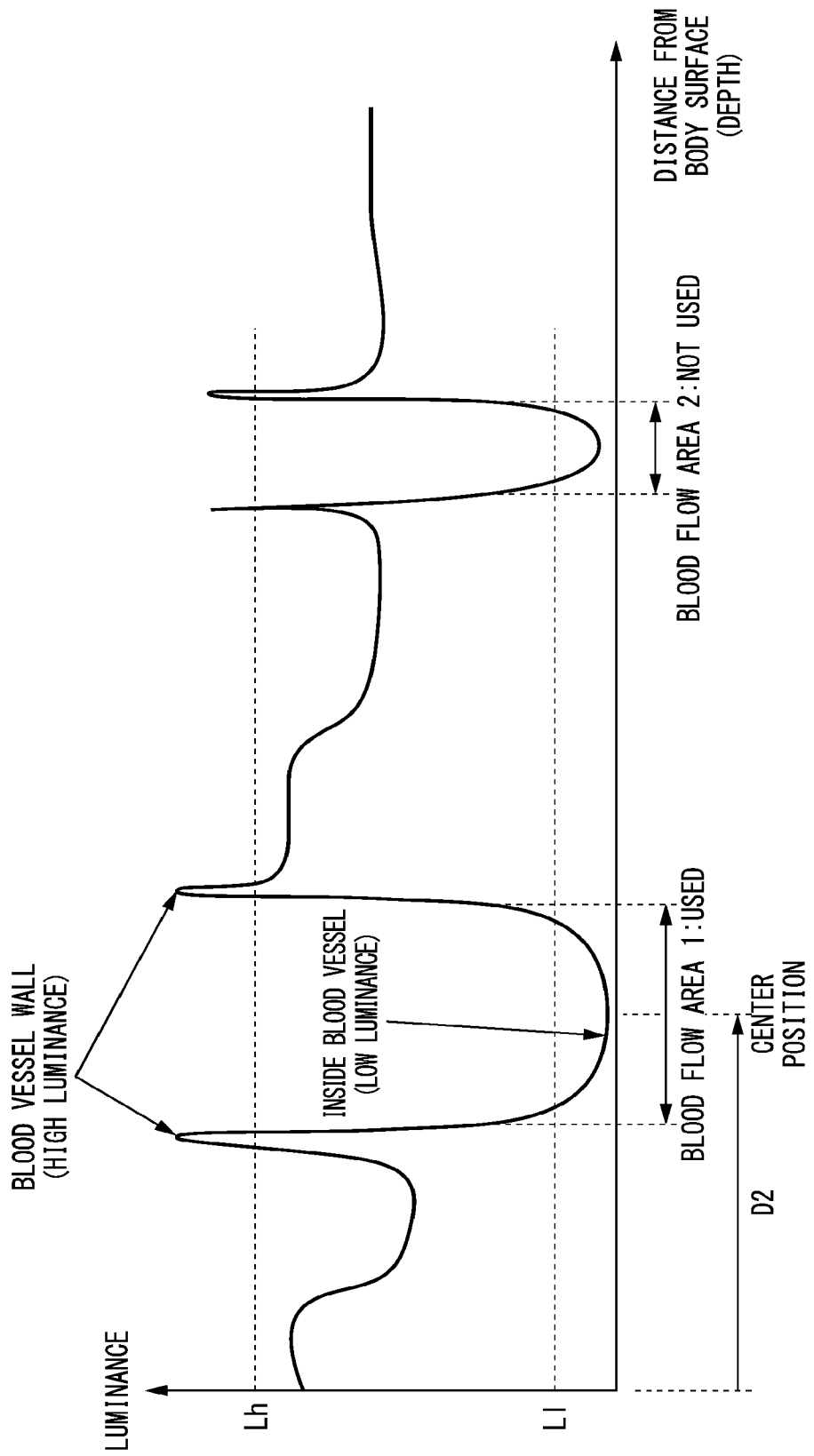
FIG. 5 is a diagram showing extraction of a blood vessel area on the basis of an additionally averaged luminance value.

FIG. 5 is a diagram showing extraction of a blood vessel on the basis of an additionally averaged luminance value. The example of FIG. 5 illustrates an example of a luminance distribution with respect to a scanning line L1 of the image IM1 illustrated in FIG. 4. As illustrated in FIG. 5, luminance values in blood vessel wall parts are higher than luminance values of other parts and luminance values in the blood vessel are lower than luminance values of other parts. Accordingly, the analysis function 164 extracts a blood vessel area by detecting a pattern having transition of high luminance to lower luminance and a pattern having transition of low luminance to high luminance in additionally averaged luminance values.

In the example of FIG. 5, when continuous transition of a luminance value from a predetermined high luminance threshold value Lh or higher to a low luminance threshold value L1 or less occurs, and then continuous transition from being less than the threshold value L1 to being higher than the threshold value Lh occurs, the analysis function 164 extracts a range between high luminance values Lh as a blood vessel area. Meanwhile, the analysis function 164 may extract, as a blood vessel area, a range between low luminance values Li or a range between average values of the high luminance value Lh and the low luminance value L1 instead of the range between the high luminance values Lh. In the example of FIG. 5, the analysis function 164 extracts blood vessel areas 1 and 2 corresponding to blood vessels V2 and V3 and extracts the blood vessel corresponding to the blood vessel area 1 closest to the probe surface of the ultrasonic probe 10 as a blood vessel that is a paracentesis target. In addition, the analysis function 164 may assume the position of the center of the range (section) between the high luminance values Lh as a center position of the blood vessel V2 and derive a distance (depth) D2 from the body surface to the center position of the blood vessel V2, for example.

In addition, the analysis function 164 derives a distance D1 or D2 with respect to Doppler image data or B mode image data in a time series and derives a variance value (value of variance with time) of the distance D1 or D2 in a predetermined time as a feature quantity indicating movement of the ultrasonic probe 10 with respect to the subject. Further, in this case, the feature quantity can also be represented as a feature quantity indicating change in the position of the blood vessel.

In addition, the analysis function 164 may acquire luminance information in B mode image data instead of the aforementioned distances D1 and D2 and derive a variance value (variance value with time) of the luminance information in a predetermined time as a feature quantity indicating movement of the ultrasonic probe 10 with respect to the subject. The luminance information may be, for example, the average luminance in the scanning area or the standard deviation of luminances. Further, the analysis function 164 may generate a histogram of luminances at each position on ultrasonic scanning lines and derive an amount of change in the generated histogram in a predetermined time as a feature quantity indicating movement of the ultrasonic probe 10 with respect to the subject. Meanwhile, a parameter indicating stability of a value with time may be a parameter other than the aforementioned variance value.

In addition, the analysis function 164 may derive a motion vector from correlation between frames of B mode images and derive information indicating the size of the derived motion vector as a feature quantity indicating movement of the ultrasonic probe 10 with respect to the subject. In this case, the analysis function 164 may identify an object included in the B mode image on the basis of a distribution of luminance information included in the B mode image, derive the motion vector of the object on the basis of a movement direction, the movement distance or the like of the object between frames continuous in a time series, and derive the size of the derived motion vector as a feature quantity indicating movement of the ultrasonic probe 10 with respect to the subject, for example. Further, the analysis function 164 may derive the size or the amount of change of the motion vector in a predetermined time.

Meanwhile, the aforementioned predetermined time for deriving a variance value or an amount of change may be variably set in response to the position, size, and the like of a target region, for example.

Hereinafter, processing in the determination function 166 will be described in detail. The determination function 166 determines whether an ultrasonic image is stable on the basis of a feature quantity analyzed by the aforementioned analysis function 164. For example, as a first determination pattern, in a case where a variance value of the distance D1 or D2 from the body surface to a center position of a blood vessel is included in feature quantities, the determination function 166 may determine that the ultrasonic image is not stable when the variance value is equal to or greater than a second threshold value TH2 and determine that the ultrasonic image is stable when it is less than the second threshold value TH2.

In addition, as a second determination pattern, in a case where a variance value of luminance information acquired from B mode image data in a predetermined time is included in feature quantities, the determination function 166 may determine that the ultrasonic image is not stable when the variance is equal to or greater than a third threshold value TH3 and determine that the ultrasonic image is stable when it is less than the third threshold value TH3.

Furthermore, as a third determination pattern, in a case where information indicating the size of a motion vector between frames of B mode images is included in feature quantities, the determination function 166 may determine that the ultrasonic image is not stable when the size of the motion vector is equal to or greater than a fourth threshold value TH4 and determine that the ultrasonic image is stable when it is less than the fourth threshold value TH4.

Meanwhile, the determination function 166 performs determination of at least one of the aforementioned first to third determination patterns. In this case, the determination function 166 may determine a determination pattern on the basis of details included in feature quantities or determine a determination pattern depending on an instruction from an operator, a type of a paracentesis target region, or the like. In addition, the determination function 166 may change values of the second threshold value TH2 to the fourth threshold value TH4 depending on a paracentesis target region, for example. When a paracentesis target region is a blood vessel near the heart or a blood vessel with a large diameter, for example, it is easily moved compared to other blood vessels. Accordingly, when a paracentesis target region is a blood vessel near the heart (within a predetermined distance from the heart) or a blood vessel with a diameter of a predetermined value or more, it is possible to determine that an ultrasonic image is stable even when slight movement occurs by increasing the second threshold value TH2 to the fourth threshold value TH4.

Hereinafter, processing in the display control function 170 will be described in detail. The display control function 170 outputs an image generated in the image generation function 168 to the display 150. For example, the display control function 170 may change a display mode of a Doppler image displayed on the display 150 using a feature quantity acquired on the basis of an ultrasonic image (at least one of a time-series B mode image and a Doppler image) acquired by the acquisition function 162.

Figure 6:
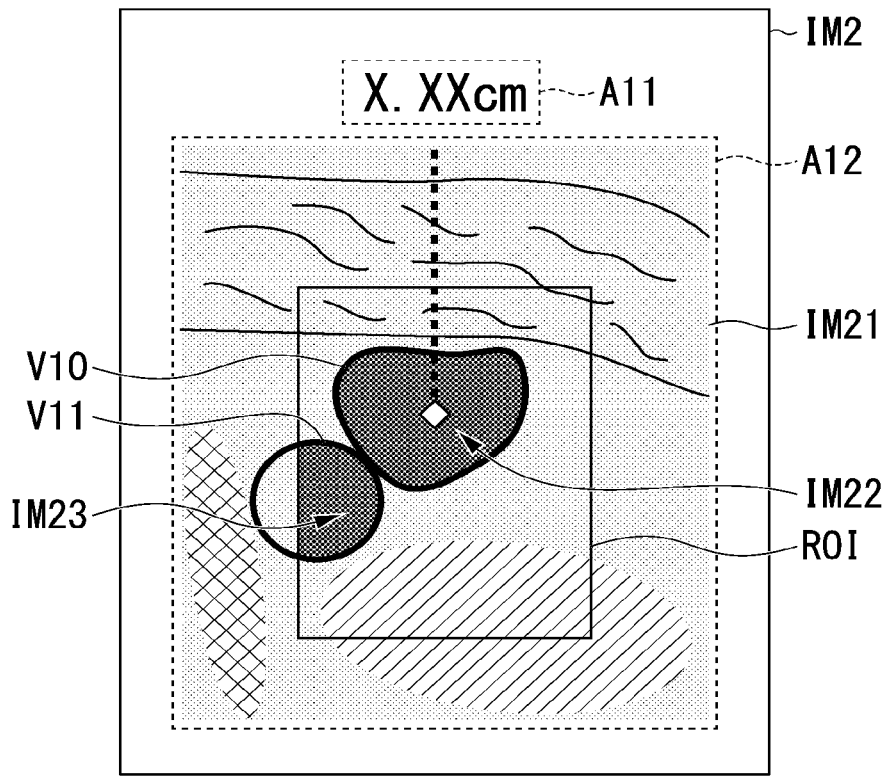
FIG. 6 is a diagram illustrating an example of an image for display in which Doppler images are superposed on a B mode image.

For example, when the determination function 166 determines that the ultrasonic image acquired by the acquisition function 162 is not stable, the current state is a state before a target blood vessel is punctured with a paracentesis needle (i.e., a state in which the ultrasonic probe 10 is moved), and thus the display control function 170 causes the display 150 to display an image for display in a display mode in which a Doppler image is superposed on a B mode image. FIG. 6 is a diagram illustrating an example of an image IM2 for display in which Doppler images are superposed on a B mode image. A layout and display details of an image for display in the embodiment are not limited thereto. The same applies to images for display which will be described below. It is assumed that a scanning area corresponding to the image IM2 includes parts corresponding to blood vessels V10 and V11.

The image IM2 may include, for example, an analysis information display area A11 and a display image display area A12. For example, information representing a distance from the body surface to a center position of the blood vessel V10 that is a paracentesis target may be displayed in the analysis information display area A11. In addition, information on a feature quantity indicating movement of the ultrasonic probe with respect to the subject, analyzed by the analysis function 164, may be displayed in the analysis information display area A11. For example, an image in which Doppler images IM22 and IM23 are superposed on a B mode image IM21 may be displayed in the display image display area A12. Further, information representing a position of an ROI and an image representing a center position of the part corresponding to the blood vessel V10 may be displayed in the display image display area A12.

As illustrated in FIG. 6, since the Doppler images are superposed in association with a blood vessel area included in the ROI of the B mode image, an operator or the like can easily recognize the area of the blood vessels and easily move the ultrasonic probe 10 such that the target blood vessel is positioned near the center of the B mode image. Furthermore, in display of images for purposes other than paracentesis, Doppler images can be displayed even in a case where the ultrasonic probe 10 is not moved.

On the other hand, when the determination function 166 determines that the ultrasonic image acquired by the acquisition function 162 is stable, the display control function 170 causes the image generation function 168 to generate an image for display and causes the display 150 to display the generated image in a changed Doppler image display mode. For example, changing a display mode of a Doppler image may be decreasing the visibility of the Doppler image. For example, decreasing the visibility of an image may be not displaying the image.

Figure 7:
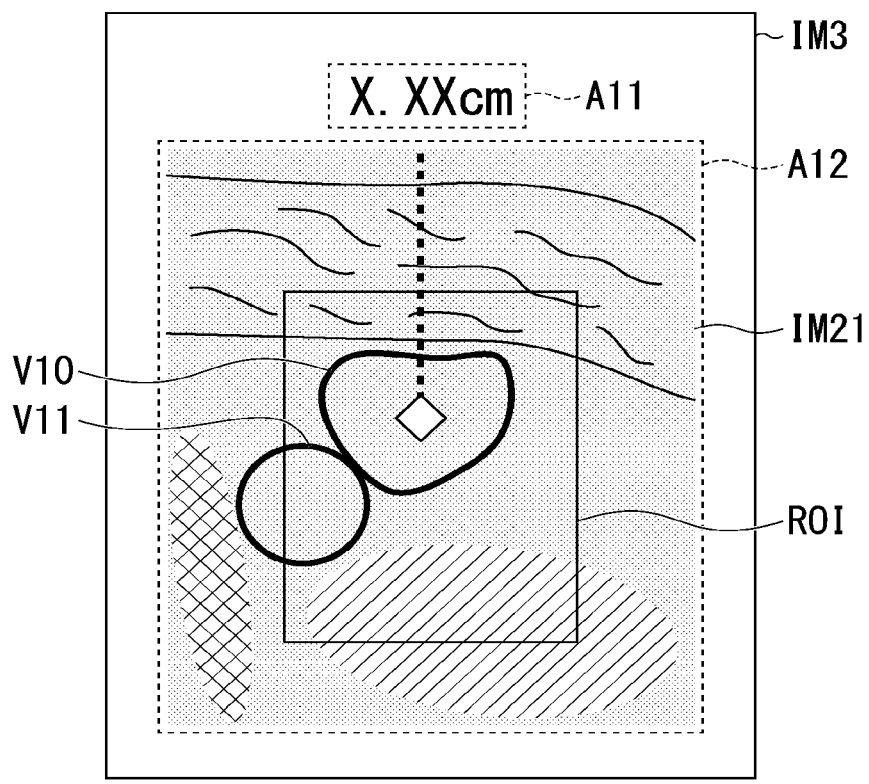
FIG. 7 is a diagram illustrating an example of an image for display in which a display state of the Doppler images has changed.

FIG. 7 is a diagram illustrating an example of an image IM3 for display in a changed Doppler image display mode. In the image IM3 for display illustrated in FIG. 7, Doppler images IM22 and IM23 are not displayed as compared to the image IM2 for display illustrated in FIG. 6. Accordingly, when the center of the blood vessel V10 that is a paracentesis target is punctured with the paracentesis needle, it is possible to curb difficulty viewing the position of the paracentesis needle or the needle tip due to the Doppler image IM22. Therefore, a practitioner can position the needle tip of the paracentesis needle at the center of the blood vessel more accurately.

In addition, the display control function 170 may change a transmission degree of the Doppler images IM22 and IM23 instead of not displaying the Doppler images IM22 and IM23. In this case, when the determination function 166 determines that the ultrasonic image is stable, the display control function 170 outputs, to the image generation function 168, an instruction for superposing Doppler images with a transmissivity increased from a transmissivity of Doppler images when it is determined that the ultrasonic image is not stable. Meanwhile, when the display control function 170 changes a transmissivity, the display control function 170 may change the transmissivity to a predetermined transmissivity or change the transmissivity to a transmissivity in response to the size or color of the Doppler image IM22. In this case, the transmissivity may be, for example, the degree of transmissivity to which a practitioner or the like is assumed to be able to visibly recognize both an image representing the paracentesis needle and the Doppler image even when both the images are displayed in a superposed manner although the visibility of the Doppler image decrease. In this manner, it is possible to visibly recognize both the Doppler image and the paracentesis needle during paracentesis by changing the transmissivity of the Doppler image.

Meanwhile, the display control function 170 may perform control such that the above-described non-display or transmission degree change of Doppler images is performed only on the Doppler image IM22 corresponding to the blood vessel V10 that is a paracentesis target. Accordingly, it is possible to enable a practitioner to easily identify a blood vessel that is a paracentesis target even in a case where a plurality of blood vessels are present in an image.

Figure 8:
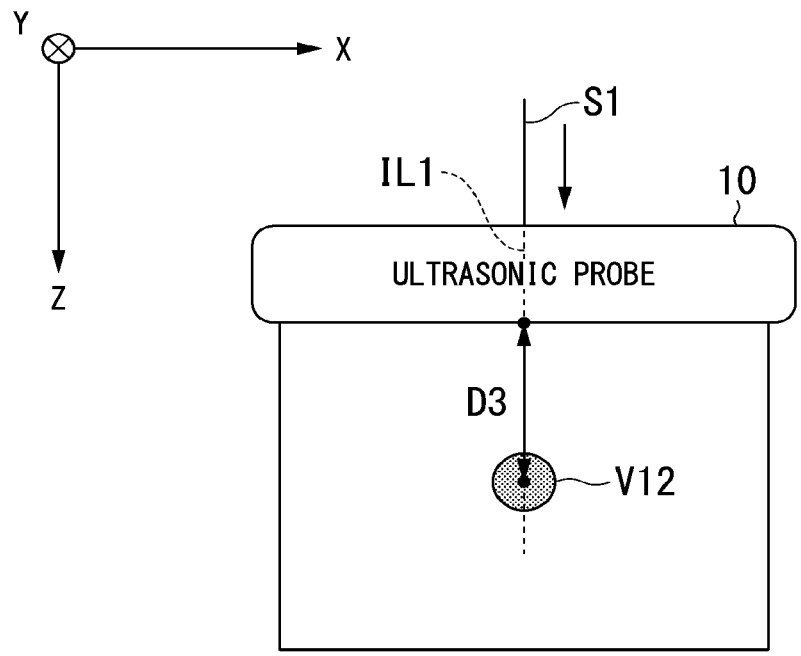
FIG. 8 is a diagram illustrating a relationship between a blood vessel and a paracentesis direction of a paracentesis needle when viewed in a cross-sectional direction of the blood vessel (Y-axis direction in FIG. 8).
Figure 9:
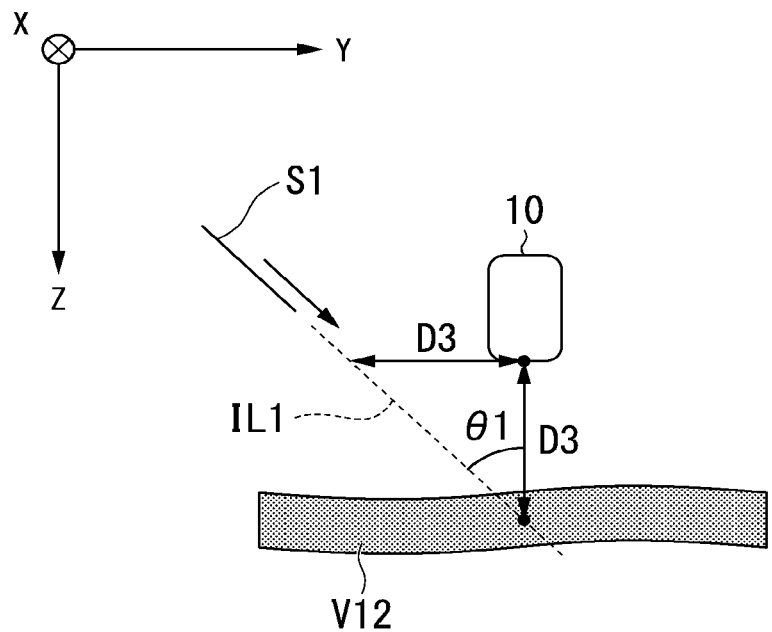
FIG. 9 is a diagram illustrating a relationship between the blood vessel and the paracentesis direction of the paracentesis needle when viewed in a direction perpendicular to the cross-sectional direction of the blood vessel (X-axis direction) illustrated in FIG. 8.

Here, a paracentesis needle puncturing method will be described using drawings. FIG. 8 is a diagram illustrating the relationship between a blood vessel V12 and the paracentesis direction of a paracentesis needle S1 when viewed in a cross-sectional direction of the blood vessel V12 (Y-axis direction in FIG. 8). FIG. 9 is a diagram illustrating the relationship between the blood vessel V12 and the paracentesis direction of the paracentesis needle S1 when viewed in a direction perpendicular to the cross-sectional direction of the blood vessel V12 (X-axis direction) illustrated in FIG. 8. In central vein paracentesis using an ultrasonic image, for example, the paracentesis direction IL1 of the paracentesis needle S1 is determined based on a distance D3 from the probe surface of the ultrasonic probe 10 to the center of the blood vessel V12, as illustrated in FIG. 8 and FIG. 9. For example, as illustrated in FIG. 9, at a position separated by the same distance as the distance D3 in a direction corresponding to the horizontal direction of the probe surface of the ultrasonic probe, in which the blood vessel V12 stretches (Y-axis direction in FIG. 9), the paracentesis needle S1 is inserted into the body at an angle θ1 with respect to an axis (Z axis in FIG. 9) perpendicular to the blood vessel V12 to puncture the blood vessel V12. The angle θ1 may be, for example, degrees, but it is not limited thereto.

Next, operations of the ultrasonic diagnostic apparatus 100 when central vein paracentesis is performed will be described. First, a practitioner who is an operator places a patient at a position suitable for paracentesis. When the patient is placed, the practitioner instructs the ultrasonic diagnostic apparatus 100 to execute a program according to the present embodiment through the input interface 140. The processing circuitry 160 of the ultrasonic diagnostic apparatus 100 reads the program according to the present embodiment from the storage circuitry 180 according to the aforementioned instruction and executes the read program.

The practitioner performs pre-scanning of veins while moving the ultrasonic probe 10 and positions a vein that is a paracentesis target near the center of an ultrasonic image. Pre-scanning includes scanning for collecting B mode image data and scanning for collecting Doppler image data. The B mode image data is collected with respect to a scanning area and the Doppler image data is collected with respect to an ROI set within the scanning area. Ultrasonic waves transmitted from the ultrasonic probe 10 to the patient are sequentially reflected by tissues in the body of the patient and received by the ultrasonic probe 10 as a reflected wave signal. The ultrasonic reception circuitry 112 performs various types of processing on the reflected wave signal received by the ultrasonic probe 10 to generate a reception signal. The signal processing circuitry 120 generates B mode image data and Doppler image data on the basis of the reception signal received from the ultrasonic reception circuitry 112 and outputs the generated data to the processing circuitry 160.

Figure 10:
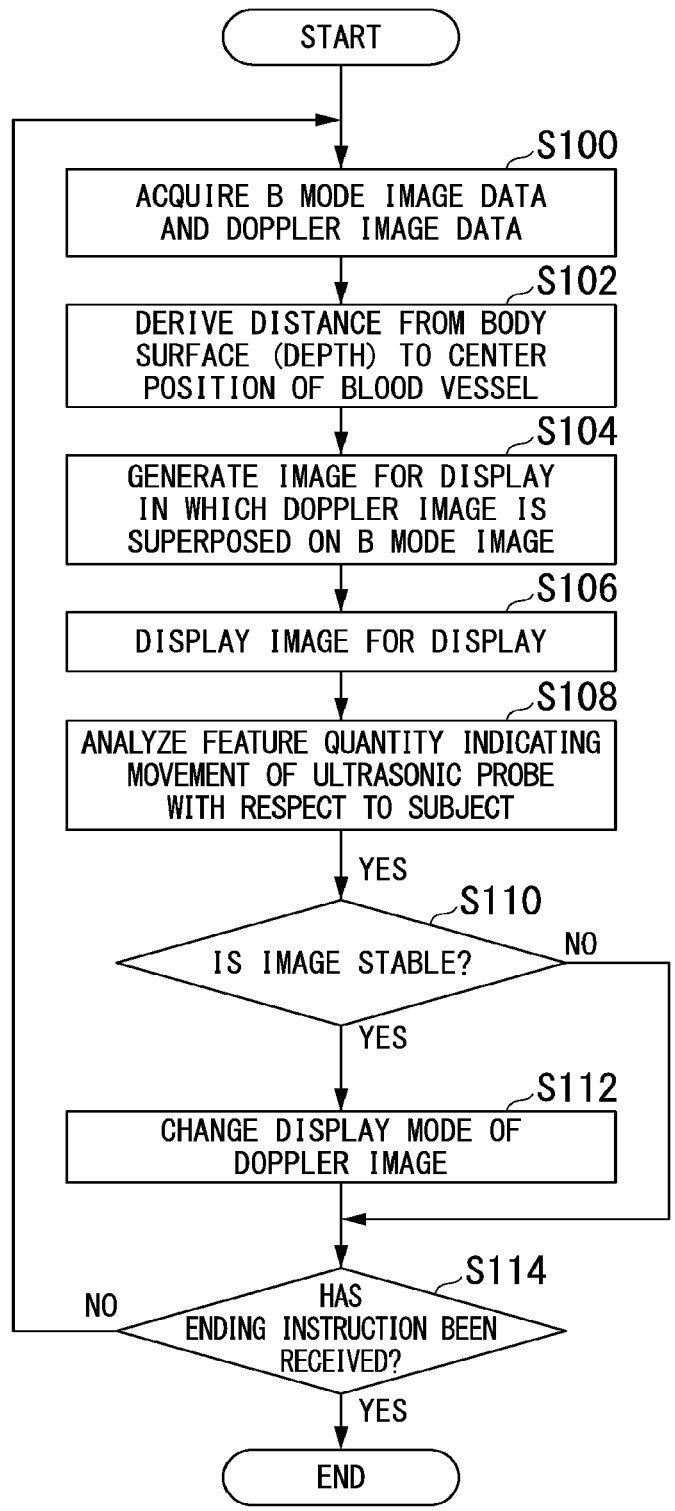
FIG. 10 is a flowchart illustrating an example of a processing flow executed by a processing circuitry.

The processing circuitry 160 executes various types of processing using the data input from the signal processing circuitry 120. FIG. 10 is a flowchart illustrating an example of a processing flow executed by the processing circuitry 160. In the example of FIG. 10, the acquisition function 162 of the processing circuitry 160 acquires B mode image data and Doppler image data (step S100). Next, the analysis function 164 derives a distance (depth) from the body surface of a patient to the center position of a blood vessel on the basis of the Doppler image data (step S102). In the process of step S102, the distance (depth) from the body surface of the patient to the center position of the blood vessel may be derived on the basis of the B mode image data instead of (or in addition to) the Doppler image data.

Next, the image generation function 168 generates a B mode image based on the B mode image data and a Doppler image based on the Doppler image data and generates image data for display in which the Doppler image is superposed on the B mode data (step S104). Next, the display control function 170 causes the display to display the generated image for display (step S106).

Next, the analysis function 164 analyzes a feature quantity indicating movement of the ultrasonic probe 10 with respect to the subject (step S108). Next, the determination function 166 determines whether the ultrasonic image is stable on the basis of the analyzed feature quantity and the like (step S110). When it is determined that the ultrasonic image is stable, the display mode of the Doppler image is changed (step S112).

After the process of step S112 ends or when it is determined that the ultrasonic image is not stable in the process of step S110, the display mode of the Doppler image superposed on the B mode image is maintained. Thereafter, the processing circuitry 160 determines whether an ending instruction has been received through the input interface 140 (step S114). When it is determined that the ending instruction has not been received, processing returns to the process of step S100. In addition, when it is determined that the ending instruction has been received, processing of this flowchart ends.

According to at least one embodiment described above, the acquisition function 162 that acquires a B mode image in which a signal intensity of reflected waves obtained in such a manner that ultrasonic waves are transmitted to a scanning area in a subject and reflected in the subject is represented by luminance levels, and a Doppler image of a region of interest included in the scanning area, and the display control function 170 that causes the display 150 to display the Doppler image superposed on the B mode image acquired by the acquisition function 162 are provided, and the display control function 170 can display an ultrasonic image in an appropriate display mode during paracentesis by changing a display mode of a Doppler image displayed on the display 150 using a feature quantity acquired on the basis of at least one of the B mode image and the Doppler image in a time series acquired by the acquisition function 162.

In addition, according to at least one embodiment, in a case where an ultrasonic image is displayed to support central vein paracentesis, for example, it is possible to enable a practitioner or the like to easily recognize positions of blood vessels and easily adjust the position of the ultrasonic probe by displaying a Doppler image superposed on a B mode image in a step of searching for a blood vessel that is a paracentesis target while moving the ultrasonic probe 10. Furthermore, since the Doppler image is not displayed or a transmission degree of the Doppler image is adjusted in a step of puncturing the blood vessel with the paracentesis needle, it is possible to easily position the paracentesis needle at the center position of the blood vessel without decreasing the visibility of the paracentesis needle in the blood vessel included in the image. According to at least one embodiment, switching between display and non-display of a Doppler image can be performed even in a case where practitioner's hands are full during paracentesis, and thus the workload of the practitioner or the like can be reduced.

Meanwhile, the processing circuitry 160 of the present embodiment may determine an operating mode in the ultrasonic diagnostic apparatus 100 on the basis of contents of an operation (e.g., an operation of selecting an operating mode such as a paracentesis mode) of an operator input through the input interface 140, perform the above-described display control in a first operating mode (e.g., paracentesis mode) and perform control such that the above-described display control is not executed in a second operating mode (e.g., a mode other than the paracentesis mode). Accordingly, a Doppler image display mode can be changed on the basis of an operating mode, and thus, for example, a Doppler image can be superposed on a B mode image and displayed even in a state in which the ultrasonic probe 10 is not moved (i.e., a state in which an ultrasonic image is stable), for example, when the ultrasonic image is displayed for a purpose other than paracentesis.

Therefore, it is possible to display an ultrasonic image in a more appropriate display mode depending on the purpose.

Any of the above-described embodiments can be represented as follows.

An ultrasonic diagnostic apparatus including:
a storage which stores a program; and
a processor,
wherein the processor is configured to, by executing the program:
acquire a B mode image in which a signal intensity of reflected waves obtained in such a manner that ultrasonic waves are transmitted to a scanning area in a subject and reflected in the subject is represented by luminance levels, and a Doppler image of a region of interest included in the scanning area;
cause a display to display the Doppler image superposed on the acquired B mode image; and
change a display mode of the Doppler image displayed on the display using a feature quantity obtained on the basis of at least one of the acquired B mode image and Doppler image in a time series.

Although several embodiments of the present invention have been described, these embodiments have been suggested as examples and are not intended to limit the scope of the invention. These embodiments can be implemented in other various forms and various omissions, substitutions and modifications are possible without departing from essential characteristics of the invention. These embodiments and modifications thereof are included in the scope and essential characteristics of the invention and also included in the invention disclosed in the claims and the equivalents thereof.

What is claimed is:

1. An ultrasonic diagnostic apparatus configured to puncture a tool into a blood vessel in a subject, comprising:
processing circuitry configured to:
acquire a B mode image in which a signal intensity of reflected waves obtained in such a manner that ultrasonic waves are transmitted to a scanning area in the subject and reflected in the subject is represented by luminance levels, and a Doppler image of a region of interest included in the scanning area;
cause a display to display the Doppler image superposed on the B mode image acquired;
in a case that a probe that transmits the ultrasonic waves is moved to identify a punctured blood vessel positioned within a predetermined distance from a center of the scanning area change a display state of the Doppler image displayed on the display using a feature quantity indicating a change in distance from a body surface of the subject depending on movement of the probe obtained on the basis of at least one of the B mode image and the Doppler image in a time series acquired; and
determine whether the probe is stable on the basis of the feature quantity, wherein
in a case that the processing circuitry determines that the probe is stable, the processing circuitry is configured to decrease visibility of the Doppler image displayed on the display to be lower than a visibility when the probe is not stable.

2. The ultrasonic diagnostic apparatus according to claim 1, wherein
the processing circuitry is configured to control the Doppler image displayed on the display such that the Doppler image is not displayed on the basis of the feature quantity.

3. The ultrasonic diagnostic apparatus according to claim 1, wherein
the processing circuitry is configured to change a degree of transmission of the Doppler image displayed on the display on the basis of the feature quantity.

4. The ultrasonic diagnostic apparatus according to claim 1, wherein
the feature quantity is derived on the basis of an amount of change of a distance from the body surface of the subject to a center of the punctured blood vessel on the basis of the B mode image or the Doppler image.

5. The ultrasonic diagnostic apparatus according to claim 1, wherein
the feature quantity is derived on the basis of a variance value with time of luminance information acquired from the B mode image.

6. The ultrasonic diagnostic apparatus according to claim 1, wherein
the feature quantity is derived on the basis of information representing a size of a motion vector derived from correlation between frames of the B mode image.

7. The ultrasonic diagnostic apparatus according to claim 1, wherein the processing circuitry is further configured to:
in a case of the Doppler image, extract the punctured blood vessel based on an average power value of blood flow on the ultrasonic scanning line, and derive a first distance from the body surface of the subject to the center position of the punctured blood vessel,
in the case of the B-mode image, extract the blood vessel by transition of luminance based on an additionally average value of the luminance value on the ultrasonic scanning line, and derive a second distance from the body surface to the center position of the punctured blood vessel, derive the feature amount based on a derived variance value of the first distance or the second distance at a predetermined time.

8. The ultrasonic diagnostic apparatus according to claim 1, wherein the processing circuitry is further configured to:

determine a determination pattern for determining whether or not the probe is stable according to an instruction from an operator of the probe or a type of the punctured blood vessel included in the scanning area.

9. A computer-readable non-transitory storage medium storing a program causing an ultrasonic diagnostic apparatus configured to puncture a tool into a blood vessel in a subject to:

acquire a B mode image in which a signal intensity of reflected waves obtained in such a manner that ultrasonic waves are transmitted to a scanning area in a subject and reflected in the subject is represented by luminance levels, and a Doppler image of a region of interest included in the scanning area;

cause a display to display the Doppler image superposed on the acquired B mode image;

in a case that a probe that transmits the ultrasonic waves is moved to identify a punctured blood vessel positioned within a predetermined distance from a center of the scanning area, change a display mode of the Doppler image displayed on the display using a feature quantity indicating change in distance from a body surface of the subject depending on movement of the probe obtained on the basis of at least one of the acquired B mode image and Doppler image in a time series;

determine whether the probe is stable on the basis of the feature quantity; and in a case that the probe is stable, decrease visibility of the Doppler image displayed on the display to be lower than a visibility when the probe is not stable.

* * * * *